(12) United States Patent
Franetzki (10) Patent No.: US 6,379,149 B1
(45) Date of Patent: Apr. 30, 2002

(54) DENTAL TREATMENT AREA

(76) Inventor: Manfred Franetzki, Nussallee 9, Bensheim (DE), D-64625

( * ) Notice: Subject to any disclaimer, the term of this patent is extended or adjusted under 35 U.S.C. 154(b) by 0 days.

(21) Appl. No.: 09/764,989

(22) PCT Filed: May 22, 2000

(86) PCT No.: PCT/EP00/04653

§ 371 Date: Jan. 22, 2001

§ 102(e) Date: Jan. 22, 2001

(87) PCT Pub. No.: WO00/71071

PCT Pub. Date: Nov. 30, 2000

(30) Foreign Application Priority Data

May 21, 1999 (DE) .......................................... 199 23 564

(51) Int. Cl.⁷ .............................................. A61C 15/00
(52) U.S. Cl. ............................ 433/77; 433/27; 433/114
(58) Field of Search .............................. 433/27, 77, 98, 433/114

(56) References Cited

U.S. PATENT DOCUMENTS

| 3,109,238 | A | | 11/1963 | Marks |
| 4,173,828 | A | | 11/1979 | Lustig et al. |
| 4,355,977 | A | * | 10/1982 | Ota et al. ................... 433/131 |
| 5,286,192 | A | | 2/1994 | Dixon |
| 5,352,118 | A | | 10/1994 | Franetzki et al. |
| 5,902,105 | A | * | 5/1999 | Uejima et al. ............ 433/77 X |

FOREIGN PATENT DOCUMENTS

| DE | 195 20 765 | 12/1995 |
| EP | 0 547 468 | 4/1997 |
| JP | 11-33037 | 2/1999 |

* cited by examiner

Primary Examiner—Nicholas D. Lucchesi
(74) Attorney, Agent, or Firm—Jacobson Holman, PLLC (57) ABSTRACT

The invention relates to a preparation unit for tubeless and cordless dental treatment appliances such as handpieces or the like which comprise at least one charging device that is connected to a pressure source for flowable media in order to charge the treatment appliances.

11 Claims, 7 Drawing Sheets

DENTAL TREATMENT AREA

The invention relates to a dental treatment and processing unit for especially hoseless and cordless handpieces or the like, which contain at least one reservoir for a cooling medium for the treatment site and at least one energy source.

Dental treatment stations of the type under discussion have been known for a long time from everyday practice and exist in varying forms of construction. For example, handpieces are operated with turbines and/or air motors and/or electric motors, in particular for drilling, milling and abrading. Furthermore, curing lights are often used. Both for operating and for cooling these components, larger quantities of air are required. In particular, a large quantity of air is required for cooling the processing site in or on the tooth by means of a spray containing a lot of air. To this end, an efficient compressor is, first of all, necessary. Furthermore, heavy duty suction machines and separating devices are also necessary to separate the waste water and the outgoing air. In many countries it is also necessary to remove the environmentally harmful mercury, thus the amalgam, from the waste water.

To supply specifically the handpiece(s), assigned to the treatment station, with the operating mediums, which are required for their operation—for example electric energy, gas or liquid—, which are fed over hose and/or cable connections from the supply units to the handpieces, a very complicated configuration and supply of the treatment station is necessary. Furthermore, owing to the complexity, the treatment station is very expensive.

Starting from the processing unit, according to the U.S. Pat. No. 5,286,192, the invention is, therefore, based on the problem of providing a dental treatment station, where a simple, compact, ergonomically optimal and inexpensive construction with a very simple supply and disposal arrangement is realized.

In the case of the said treatment and processing unit, the invention provides that the treatment station includes means that enable the usual patient treatment of drilling, abrading, cleaning with the feed and removal of cooling mediums and the processing of the waste water under optimal hygienic and ergonomic conditions without a hose connection to the suction machine, compressor, tap water and waste water lines. At the same time the relatively low flow rate of cooling water, which is introduced into a patient's mouth, is utilized, as described in the document EP B 547 468. Thus, the goal is reached that the treatment site of the patient, thus in particular the treatment chair and its environment, can be kept completely free ofconnections for flowing mediums, such as air and water, and their drain lines, and of the electrical cables.

Expediently the handpieces within reach of the physician are disposed preferably on a tray. Furthermore, it is advantageous if a processing unit (charging unit) is available that charges the handpieces by means of couplings with the cooling mediums and electric energy. The invention can be designed especially advantageously to the effect that in the processing unit the cleaning and/or the disinfecting and/or the sterilization and/or the lubrication and/or other care of the handpieces occurs/occur. It is advantageous for a charging unit for the hoseless and cordless handpieces to be attached to a pressure source for air and/or a pressure source for water and/or to a waste water line.

Expediently the charging unit is supplied with electricity and attached to a pressure source for air and/or a pressure source for water and/or to a waste water line or generates the pressure from the surrounding air and the liquid reservoirs itself In detail, the charging unit can exhibit at least one connecting piece for receiving a counter-connecting piece of a hand unit, which is connected to the pressure source and/or to a source of electric energy for recharging the reservoirs, located in the handpiece. It is further recommended that the charging unit be coupled to a source of hot pressurized water.

In another preferred embodiment of the invention the processing unit includes a suction system with a collecting container for waste water and waste. The suction system can exhibit advantageously a canula with variable lumen. Furthermore, it is recommended that the collecting container exhibit an interchangeable filter made preferably of hydrophobic material.

In a further development of the invention the processing unit can include a separating system for separating liquids and solids, preferably amalgam. For the separating system an evaporation unit is recommended for the liquid that can be realized, for example, with a microwave generator for a mixture of liquid and solid, contained in a tank. Expediently the separating system is disposed behind a preferably microwave-proof flap. Finally the processing unit can also be designed in such a manner that there is a cuspidor, which is attached to a telescope support arm and which is assigned to a suction canula.

In an inventive manner it was recognized, first of all, that it is quite possible to use at least to some extent handpieces that are not connected to hoses or cables. In a further inventive manner at least one handpiece exhibits a reservoir for the energy and/or the gas and/or the liquid. Thus, the handpiece is supplied in a self-sufficient manner with operating mediums. The consequence is that the dental treatment station no longer requires complicated hose and/or cable connections. Furthermore, there is no need for heavy duty compressors or other supply units that normally feed operating mediums or energy over hose or cable connections to the handpieces. Thus, both the cost for the hoses, cables and couplings and for the expensive supply unit is eliminated. Finally the treatment station or the processing unit can be configured with a smaller space requirement.

Consequently the treatment station of the invention provides a treatment station, where a simple, compact and inexpensive construction is realized.

Depending on the requirement, the gas can be air, and/or the liquid can be water. Air and/or water constitute especially good coolants for a treatment site. For cooling, a spray, containing a lot of air, is used with water in the conventional manner. However, the results are that large quantities of water to be disposed collect, whereby the bulk of the water does not directly reach the treatment site to be cooled as spray, but rather is sprayed unused on the areas surrounding the treatment site. The air carries the generated aerosol cloud into the treatment space and contaminates it.

As an alternative to spray cooling, a pure liquid cooling arrangement could be used, where the liquid, for example water, is guided directly to the treatment site. For the cooling effect, it is only the water and not the air that is effective owing to its comparatively low thermal capacity. Since the liquid can be aimed better at the treatment site, a significantly smaller volume of liquid has to be used as compared to spray cooling for a comparable effect. Therefore, the consequence of such a pure liquid cooling arrangement is also a significantly smaller volume of liquid to be disposed. This feature reduces the number of equipment for draining and disposing the liquid.

In the case of cooling the treatment site largely without air, for example by means of pure liquid cooling, air is often required only in small quantities for cooling motors, as chip blowers, or for drying a tooth. Thus, expensive compressors can be avoided and the medium—air—can be reduced to a minimum.

With respect to an especially compact and multifaceted storage of a gas or a liquid, the reservoir could be a pressure and/or thermo-container. Thus, it is possible to feed a prethermostatted operating and/or cooling medium to the treatment site. The design of the handpiece(s) with a reservoir for the operating and/or cooling medium makes it possible to operate the handpieces without continuously supplying the handpieces by means of a cable or hose connection.

The treatment station, according to the invention, could exhibit a suction system for exhausting air and/or saliva and/or debris. With the use of pure liquid cooling, the suction system can be dimensioned significantly smaller than the conventional suction systems using spray cooling. The quantity of coolant, which accumulates in the mouth during liquid cooling, can be removed with a suction system that exhibits only the capacity of a conventional saliva ejector. Since the accumulated drill debris requires a higher suction capacity and optionally larger lumina of the suction canula than the saliva ejector offers, the suction system could be designed to operate at least two differently dimensioned canulas and/or with different suction capacities. To remove the drill debris or for other special functions, a second larger canula could be inserted temporarily into the same suction hose and/or the suction capacity could be increased for a short period of time. The increase could occur automatically owing to the larger volume of the larger suction canula or be switched by means of an operating element. As an alternative to the two differently designed canulas, the suction system could exhibit a canula with variable lumen. In this respect the canula could be flexible to such a degree that in the bent state it enables a smaller volume of suction then in the stretched state. In the bent state it could serve as the saliva ejector and in the stretched state it could serve as the suction canula for the drill debris.

To generate the vacuum, required for the removal by suction, the suction system could exhibit a pump or a blower. With respect to the ability to adapt to the varying suction requirements, the pump or the blower could exhibit at least two switchable performance steps.

The canula could be connected by means of a connector, preferably a hose, to a container. The pump or the blower could be assigned to the container in a manner that is especially effective for removal by suction. Thus, the losses with respect to the suction capacity via hoses and the like are avoided. Following removal of the canula from its holder, the pump or the blower—in the simplest case a ventilator—could start automatically; and the air, saliva, coolant and debris, for example drill debris, amalgam, etc., could be removed by suction into the container. To exhaust the air, the container could be assigned an air permeable, preferably interchangeable filter. The container could be closed at the top with the filter. The filter could permit air to flow through, but not the coolant, bacteria and other particles.

In an especially hygienic and simple manner the filter could be made of a hydrophobic material. The filter could be made of a fine mesh screen, for example polypropylene.

In an especially practical manner the container could be removeable from the suction system. Thus, it could be taken out of the suction system or taken from the suction system, when it is filled. Finally the container could be disposed in a manner that is typical of the trade and/or customary in the country. In this respect disposal as special waste over separate amalgam separators into a drain, a toilet or garbage can is conceivable. Finally a replacement container or the emptied container could be assigned again to the suction system. In an especially practical manner the suction system could be attachable to an arm to hold a tray for, for example, dental instruments. In particular the container and the pump or the blower could be attachable to the tray arm. In its resting position the canula, either a single canula or a canula that can be switched over to a higher suction capacity, could be suspended from the suction system.

As an alternative or in addition, the treatment station could exhibit a separating system for separating liquids and solids, especially amalgam. In the past sedimentation containers, centrifuges and for larger particles—screens—have been used to separate amalgam. Owing to their operating principle, these separators are especially suitable when solids are conveyed in larger quantities of coolant. All of these principles can, of course, also be used with smaller quantities of coolant, thus also in treatment stations, described here.

In operating a treatment station with a small quantity of coolant, however, still other disposal methods could be applied. First of all, solids can be disposed together with the coolant. Furthermore, filtering could be done over a correspondingly fine filter. Since filters clog very rapidly with biological liquid, filters for continuously working amalgam separators are not very suitable. In contrast, disposable filters are quite appropriate. For example, the collected coolant or waste water with solids could be cleaned over a filter, which can be similar to a coffee filter. In so doing, only the coolant could be allowed to flow through. Or the coolant could be accelerated by means of suction or pressure. Then the cleaned coolant flows into the drain, whereas the filter is periodically removed and disposed with the content.

Another possibility is to evaporate the liquid. Especially when the volume of liquid is not too large, it is possible and logical to concentrate the scum by evaporation. In so doing, the collecting container is emptied into another larger container. The separating system could exhibit an evaporator, where a heating spiral or a microwave generator could be provided as the evaporator. Thus, the liquid is heated; and the water or the coolant and/or rinse medium is evaporated.

The steam could be led into the drain. To this end, there could be a ventilator. The drain could be provided with a check valve, which prevents the odors from escaping to the outside. When the evaporation container is filled, it is removed, closed and disposed. As an alternative, only its dry content could be disposed.

To dry a treatment site, there could be a handpiece, to which a drier is assigned. In this respect the drier could be integrated into the handpiece or be attached to the handpiece so as to be detachable. What is important here is that the handpiece can be operated semi-independently and not exhibit any obligatory hose and/or cable connections to a supply unit.

With respect to an especially effective drying process, the drier could exhibit an electrically operated hot air blower. The electricity could be supplied to the hot air blower by means of a suitable storage for electric energy, for example an accumulator. As an alternative or in addition, the drier could exhibit a device for emergency operation. In this respect the handpiece could be used as a chip blower.

The dental treatment station could exhibit a handpiece with a two medium syringe, which is assigned to the handpiece and exhibits a reservoir for a liquid and a gas. The two medium syringe could be integrated into the handpiece or be attached to the handpiece so as to be detachable. The gas could be air, and/or the liquid could be water.

Thus, a gas and liquid supply could be realized in a simple manner. Here, too, it is important that the handpiece can be operated semi-independently.

In an especially practical design, the drier and the two medium syringe could be assigned to one and the same handpiece.

The drier and the two medium syringe could be attached to the handpiece or be integrated into the handpiece.

Finally the drier could be a cableless hot air blower, similar to a hot air fan, whose exterior can be disinfected or sterilized. There could be a hoseless water and air syringe, which contains rechargeable reservoirs for water, air and optionally electric energy. There could also be operating elements, which switch separately or mixed the delivery of the mediums.

The treatment station could exhibit an electrosurgical handpiece and/or a curing light handpiece. The rear part of the handpiece could exhibit the control electronics, operating/display elements and an electric energy storage, for example an accumulator. The energy store can be put via a coupling on a connecting piece for recharging.

As an alternative or in addition, a handpiece could be provided with a tooth calculus remover with a water cooling device. The water cooling device could exhibit a rechargeable reservoir and conveying equipment.

A charging unit could be provided for the handpiece(s). The charging unit could be formed by a separate device, which is disposed, for example, behind the treatment chair and thus behind the head of the patient. Thus especially short paths for recharging with operating mediums would be realized.

The charging unit could also be designed for the care and cleaning and/or disinfecting and/or sterilization of the handpieces. Furthermore, the charging unit could be designed for body temperature feed of operating mediums into the reservoir(s). It is especially advantageous for the reservoir involved to be a thermocontainer. Thus, for example, water, but also any other operating medium, could be filled at body temperature from the charging unit into the corresponding reservoirs and held there thermally insulated.

The charging unit could exhibit means that are suitable for charging the hoseless handpieces with the requisite mediums by putting on a connecting piece. Suitable mediums are, depending on the handpiece, electric energy, compressed air, and coolants, for example water. Furthermore, the charging unit could exhibit means for cooling the handpieces, in order, for example, to dissipate the lost heat of the motors. Such means could be coupled to the connecting piece.

Furthermore, the charging unit could exhibit a heater, which heats the handpieces to a specifiable temperature, for example, hand temperature.

Furthermore, the charging unit could exhibit at least one fast charging connecting piece, by means of which the gas and/or the liquid can be recharged in a very short period of time.

In an especially simple manner the dental treatment chair could exhibit only one electric connection. With the use of the handpieces, which are described above and that exhibit autarkic reservoirs for the operating mediums, not only a heavy duty compressor and a heavy duty suction machine but also the physician element with the customary hose-connected handpieces are eliminated. Furthermore, a large suction canula, today's customary automatic separating machine and expensive amalgam separators could also be dispensed with. The functions that are necessary for the treatment are maintained despite the simpler design of the treatment station, which gains an ergonomic function.

At this point there are various options for designing and improving in an advantageous manner the teaching of the present invention. On the one hand, reference is made to the claims, subordinate to patent claim 1; on the other hand, reference is made to the following explanation of two preferred embodiments of the invention with reference to the drawings. In conjunction with the explanation of the preferred embodiments of the invention with reference to the drawings, preferred designs and improvements of the teaching are explained in general.

Figure 1:
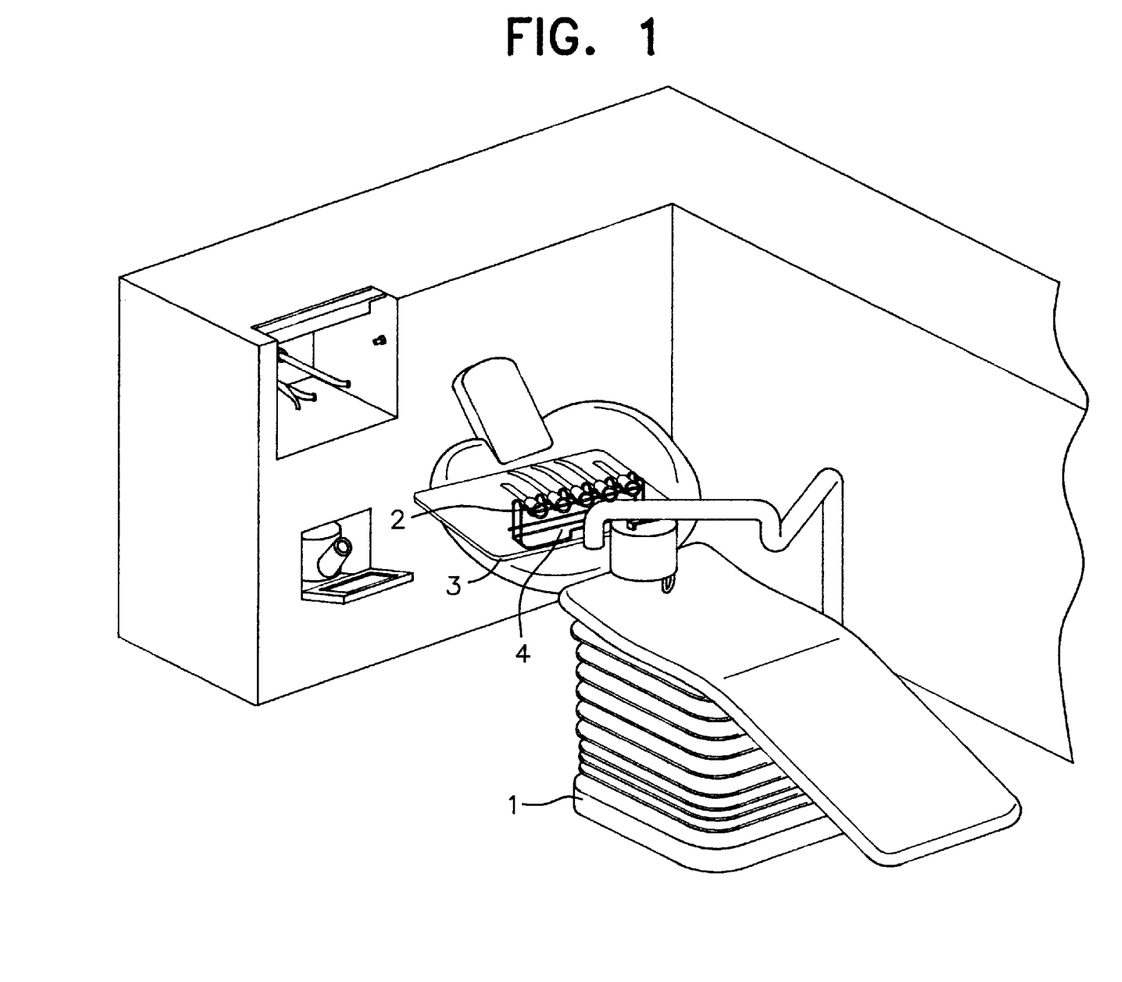
FIG. 1 is a perspective view of the first embodiment of a dental treatment station, according to the invention.

FIG. 1 is a perspective view of the first embodiment of a dental treatment station, according to the invention. The treatment station exhibits a dental treatment chair 1 for patients and several handpieces 2 for supplying the patients through dental personnel. The handpieces 2 in the form of a curing light are operated, for example, with electric energy. Furthermore, handpieces 2 are used that exhibit an autarkic gas drive for the turbine. Furthermore, handpieces 2 are used that exhibit a reservoir for, for example, coolant for the treatment site. With respect to the simple, compact and inexpensive construction of the treatment station, at least one handpiece 2 exhibits such a reservoir for the energy, gas or liquid that a hoseless and/or cableless operation is possible. This feature significantly simplifies the handling of the handpieces 2 during treatment of a patient.

The dental treatment chair 1 exhibits only electric components, thus no supply and drain lines for waste water or corresponding compressed air lines. Thus the typical physician element can be dispensed with, and the handpieces 2 can be placed on a tray 3 for treatment.

The dental treatment chair 1 is any arbitrary singular chair with only one electric connection. The requisite instruments and handpieces 2 lie on the tray or tablet 3—on a holder 4 or also without a holder 4. In the embodiment depicted in FIG. 1, it involves a motor-operated handpiece 2 for rotary tools, an ultrasonic tooth calculus remover, a curing light, a two medium syringe and a dry blower. A local suction device and the canula are suspended from the support arm. Other handpieces 2, for example, also an electrosurgical handpiece, are ready for use in the charging station. This variation does not include a cuspidor, but rather all solid and liquid parts are siphoned from the mouth. Behind the treatment chair 1, i.e. virtually behind the head of a patient, the charging, care, disinfecting or sterilization of the handpieces 2 is performed. A fast charging connecting piece, for example behind the head of the patient and perhaps in the charging station on the side on the inside wall, permits a fast recharging with air, propellant gas or coolant, should one filling be inadequate for the treatment of a patient.

Figure 2:
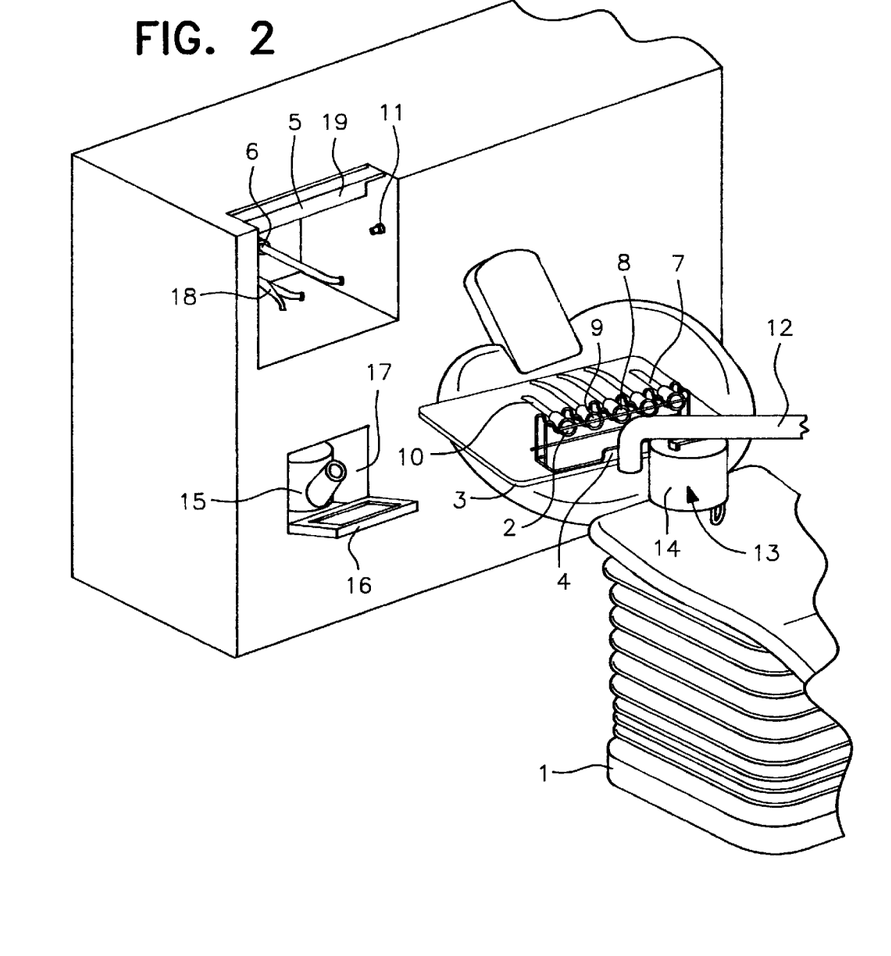
FIG. 2 is a perspective view of the treatment station from FIG. 1 in detail.

FIG. 2 is a perspective view of the treatment station from FIG. 1 in detail. Above the dental treatment chair 1 is a tray 3 for handpieces 2. Said tray exhibits a holder 4 for the handpieces 2. The handpieces 2 are supplied with their operating mediums in a charging unit 5.

Suitable handpieces 2 are an ultrasonic handpiece 6, a curing light 7, a handpiece with a drier, which is designed as a hot air blower 8, a rotary handpiece 9 and a handpiece 10 in the form of a two medium syringe. In the area of the charging unit 5, which is designed as a station for charging, caring and disinfecting or sterilizing the handpieces 2, there is also a charging connecting piece 11 for fast charging of the handpieces.

The tray 3 is hinged to a tray arm 12. Furthermore, the tray arm 12 has a suction system 13 for removing by suction the air and/or the saliva and/or the coolant and/or the debris. The suction system exhibits a container 14 for collecting the siphoned gas and the siphoned liquid and particles.

Furthermore, the treatment station exhibits a tank 15 for collecting solid and liquid waste. Said tank can also be used to evaporate the liquid. The tank 15 is disposed in a wall recess 17 that can be closed with a flap 16.

The charging unit 5 has also a large high frequency surgical device 18. The charging unit 5 can be closed with a sliding door 19.

The electrosurgical handpiece 18 and the curing light 7 exhibit in the rear part control electronics, an operating and display element and an electric energy store, for example in the form of an accumulator. It can be put via a coupling on a connecting piece for recharging. This connecting piece could be disposed in the charging unit 5. A tooth calculus remover could exhibit, in addition to the electronics and mechanism, a water cooling arrangement. Furthermore, the tooth calculus remover exhibits a reservoir for the water and conveying and charging units.

Figure 3:
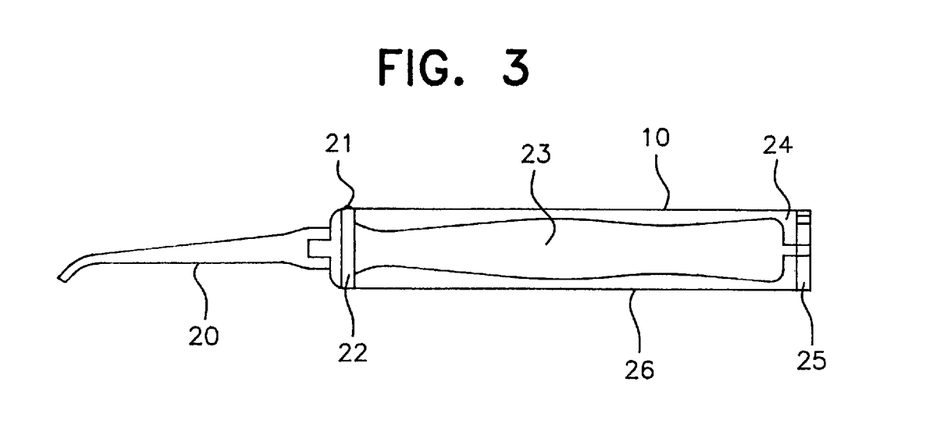
FIG. 3 is a schematic side view of an inventive handpiece in the form of a two medium syringe.

FIG. 3 is a schematic side view of a handpiece 10, designed in the form of a two medium syringe. The handpiece 10 exhibits a canula 20 for water and air. Operating elements 21 are disposed in the front part of the handpiece 10 in the area of a valve block 22. In the center of the handpiece 10 there is a water reservoir 23. The water reservoir 23 is almost completely surrounded by an air reservoir 24. In the rear area of the handpiece 10 there is a coupling 25 for charging with air and water. The water reservoir 23 and the air reservoir 24 are enclosed by a housing 26.

The handpiece 10 works without electric supply. The front part is designed analogously to a hose-supported two medium syringe. The canula 20 can be removed. The air reservoir 24 can be filled with propellant air or propellant gas, to which end the housing 28 is designed gas-tight.

Furthermore, the housing 26 is thermally insulated so that hot water, which is fed from the charging unit 5, cools only very slowly. The water and propellant air can be recharged, as desired, also during treatment by briefly sliding on the corresponding charging connecting piece 11. Optimally a heater can be built into the handpiece 10. Said heater is operated by means of an accumulator. Thus, propellant air and water can be heated. Furthermore, the handpiece 10 can exhibit illumination, which is also supplied with energy by means of an accumulator.

Figure 4:
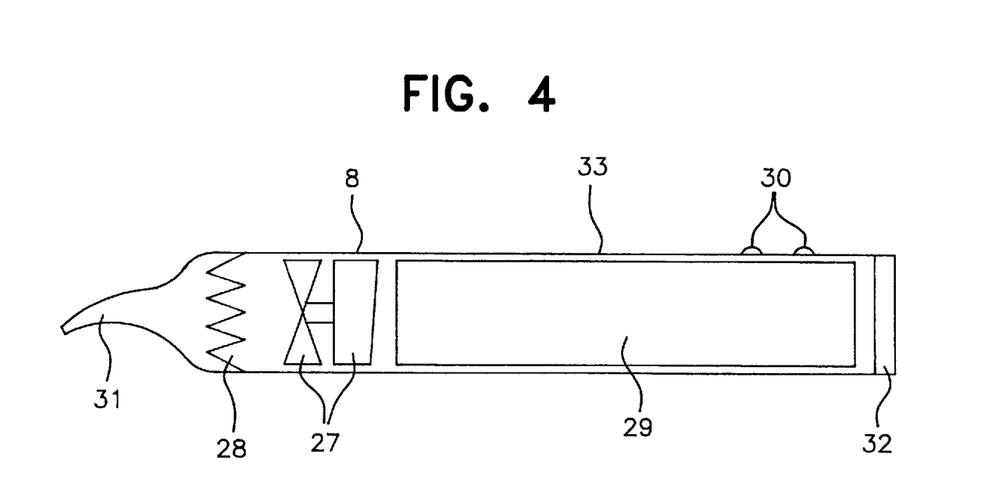
FIG. 4 is a schematic side view of an inventive handpiece with a drier.

FIG. 4 is a schematic side view of an inventive handpiece 8 with a drier. The handpiece 8 is designed as a dry blower and exhibits a ventilator 27. The construction of the handpiece 8 is virtually identical to that of a hair drier. To heat the drying air, there is a heating cartridge 28, which is supplied with energy by an accumulator 29. The handpiece 8 is operated by means of operating elements 30. The heated air issues from the outlet nozzle 31. In the rear part of the handpiece 8 there is a coupling 32 for charging the accumulator 29. All components are integrated in essence in a housing 33. As an alternative to charging the accumulator 29, it can also be exchanged for a charged accumulator.

Figure 5:
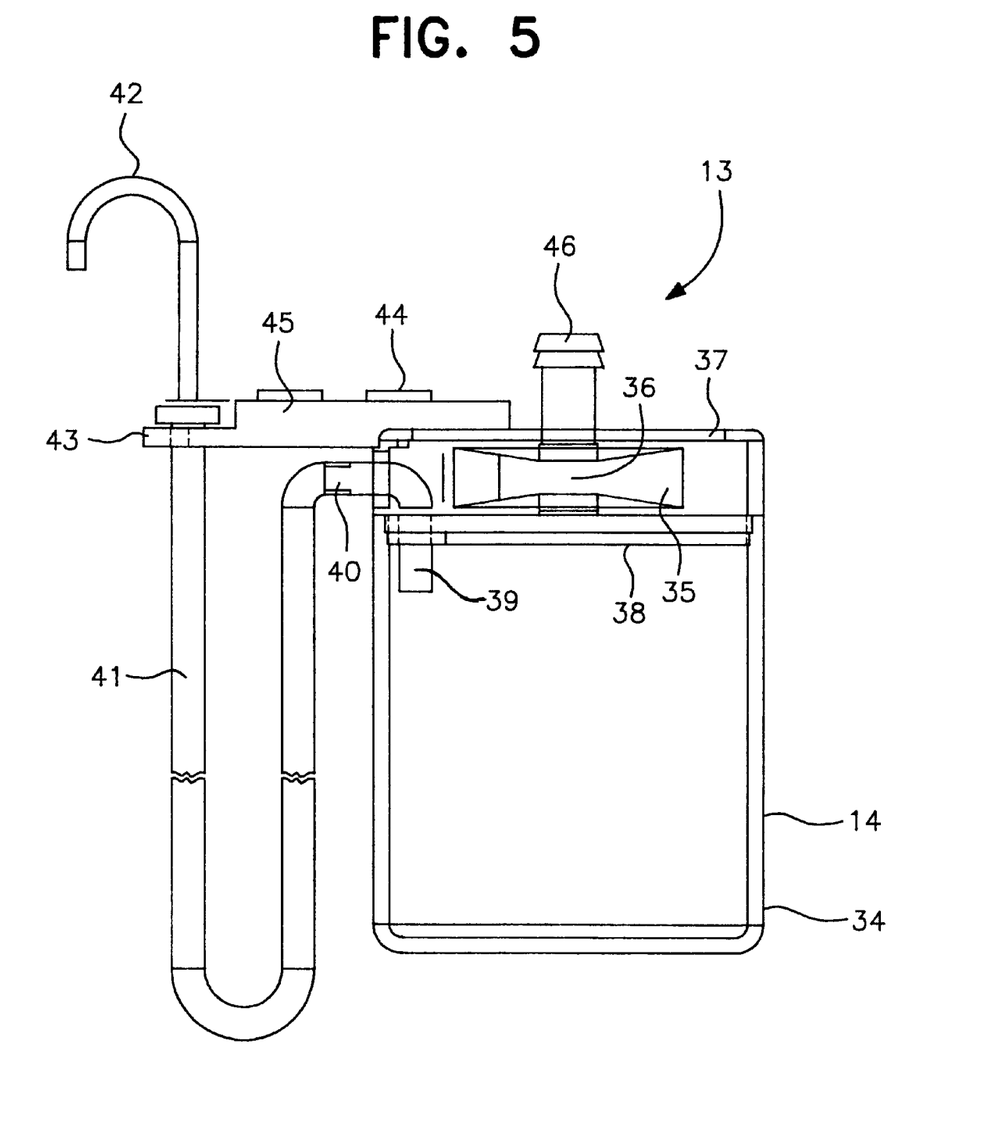
FIG. 5 is a schematic side view of an inventive suction system with container.

FIG. 5 is a schematic side view of an inventive suction system 13 with a collecting container 34 for waste water and debris.

To generate a vacuum for the suction process, the suction system 13 exhibits a suction blower blade 35, which is driven by a blower motor 36. The outlet of the blower air exhibits an outlet filter 37. Furthermore, the suction system 13 exhibits between the blower blade 35 and the collecting tank 34 a hydrophobic fine filter 38 for retaining particles of all type.

Furthermore, the container 14, designed as a collecting tank 34, is assigned a connecting adapter 39 for a suction canula 42. The suction canula 42 is connected to the connecting adapter 39 by means of a canula hose 41. Between the connecting adapter 39 and the canula hose 41 there is a connection 40. Furthermore, the suction system 13 is assigned a holder 43 for the suction canula 42. To operate the suction system 13 there are operating and/or display elements 44 and control electronics 45. Finally the suction system 13 exhibits a holding arm 46 for a separating tank, which can be connected to the tray arm 12.

Figure 6:
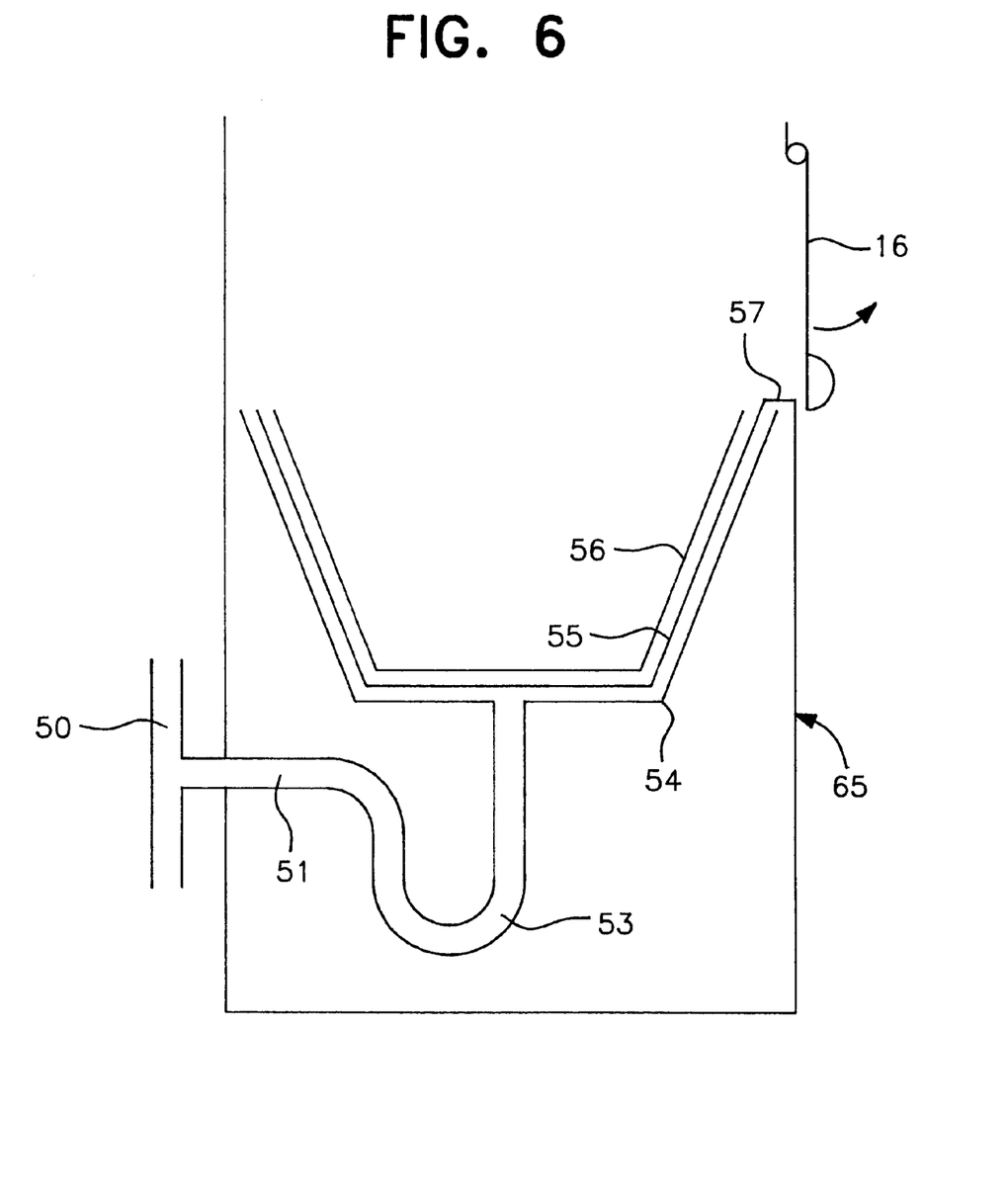
FIG. 6 is a schematic side view of an inventive separating system with a filter.

FIG. 6 is a schematic side view of an inventive separating system 65, where the liquids are separated from the solids by means of filtering. To this end, the separating system exhibits a disposable filter 56, which is positioned by means of a holder 55. The holder 55 can be removed by means of a handle 57. The holder 55 and the filter 56 are disposed in a funnel-shaped pot 54. Filtered liquid is passed through a siphon 53, serving as an odor locking mechanism, and through a feed line 51 to flow out into a drain pipe 50. The separating system is disposed behind a flap 16, which exhibits a handle and is designed odor-tight.

Figure 7:
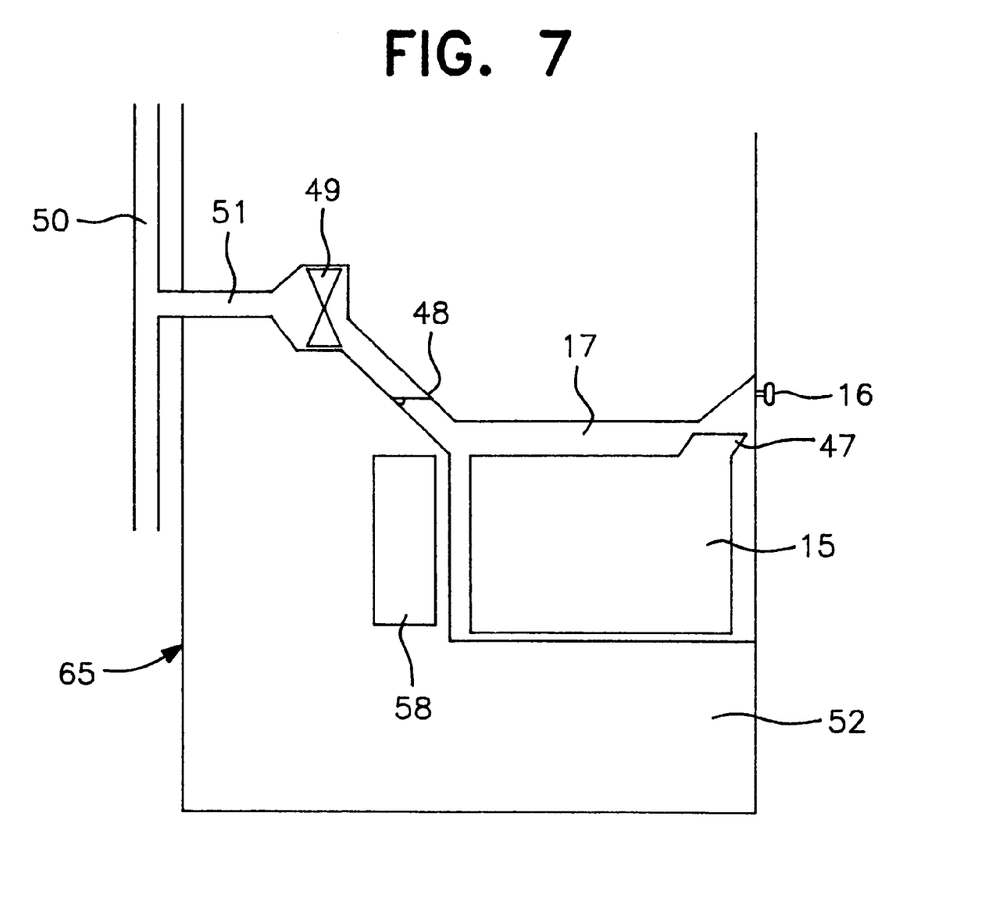
FIG. 7 is a schematic side view of an inventive separating system with an evaporation container.

FIG. 7 is a schematic side view of an inventive separating system 65 with an evaporation container or tank 15. The tank 15 is made of plastic and exhibits a fill connecting piece 47, which can be closed for the purpose of disposal. The tank 15 is disposed behind a flap 16 of a housing or cabinet 52. In this design the flap 16 is microwave-proof.

The microwaves are generated by means of a microwave generator 58 and act on the mixture comprising liquids and solids in the tank 15. Volatilized or evaporated liquid is passed into the chamber 17 and diverted into a drain pipe 50. Between the chamber 17 and the drain pipe 50 there is a check flap 48 or a valve. Furthermore, this flow path has a ventilator 49 for siphoning off the steam. Between the ventilator 49 and the drain pipe 50 there is a feed line 5 1.

Figure 8:
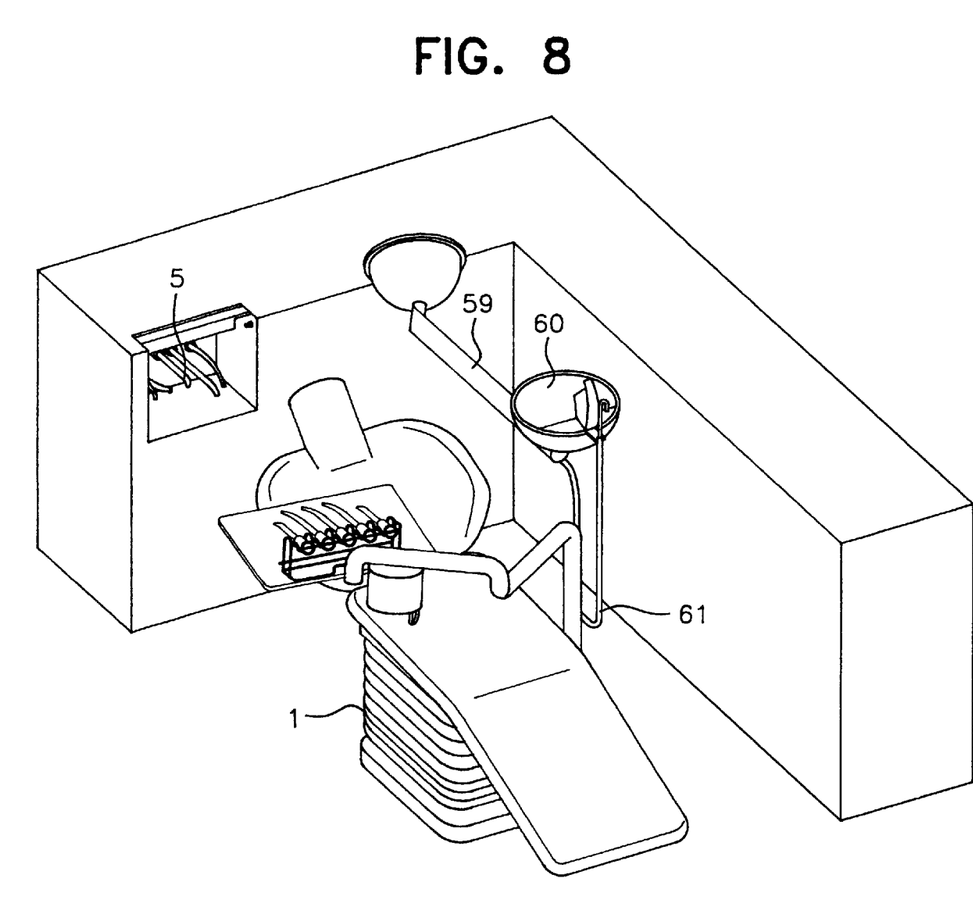
FIG. 8 is a perspective view of the second embodiment of a dental treatment station, according to the invention.

FIG. 8 is a perspective view of the second embodiment of a treatment station, according to the invention. The treatment station exhibits a cuspidor or a spittoon bowl 60 and a conventional outgoing air and waste water processing arrangement. To this end, the spittoon bowl 60 is assigned a suction canula 61. The spittoon bowl 60 and the suction canula 61 are mounted on a telescope support arm 59. Otherwise the treatment station, according to the second embodiment, is identical to the first embodiment.

The spittoon bowl 60 is pulled by the telescope support arm 59 from a cabinet. However, it can also be pulled out on a wagon; or, as in the past, it can be built into the treatment chair 1. The waste water processing is done in the cabinet or also, as described above, by filtering, whereby the filter is changed regularly or continuously by evaporation.

In an even more traditional design, not only the spittoon bowl, but also, besides the saliva ejector, a large suction canula is guided in the usual manner to the patient from the side or rear head cabinet. Similarly a conventional two medium syringe with hose can also be pulled up, and in succession curing light, video camera, etc. That would mean that the assistant works essentially tied to the hose; however, the dentist works without the hose. The air, water and solids can be supplied and disposed in the conventional manner. In an even less further developed case, only specific handpieces would be without a hose; others would be provided with hoses. The work station would have to be designed as a hybrid.

With respect to other advantageous designs and farther developments of the inventive teaching, reference is made, on the one hand, to the general part of the specification and, on the other hand, to the attached patent claims.

In conclusion, it must be emphasized that the above purely arbitrarily selected embodiments serve only to explain the inventive teaching, but do not restrict in any way the teaching to these embodiments.

What is claimed is:

1. A dental treatment station comprising a plurality of handpieces, each of which are hoseless and cordless, and each of which include at least one reservoir for a cooling medium for a patient treatment site, and each of which include at least one energy source, said dental treatment station further comprising a charging unit including means for recharging the handpieces with at least the cooling medium, and a tray for temporarily receiving at least one of said handpieces.

2. A dental treatment station as claimed in claim 1 further comprising a suction system for separating air from liquid and solid material drawn from a patient.

3. A dental treatment station as claimed in claim 1 wherein said charging unit includes means for recharging the handpieces with at least one of electric energy and pressurized air.

4. A dental treatment station as claimed in claim 1 wherein said charging unit includes at least one of an air pressure source and a water pressure source.

5. A dental treatment station as claimed in claim 1 wherein said station includes a patient chair and a cabinet, said charging units accommodated within said cabinet.

6. A dental treatment station as claimed in claim 5 wherein said charging unit is hidden by a window shade.

7. A dental treatment station as claimed in claim 1 further comprising a collecting container for waste water and debris.

8. A dental treatment station as claimed in claim 7 wherein said collecting container comprises a cannula with a variable lumen such that said cannula exhibits a smaller suction volume in a bent state than in a stretched state.

9. A dental treatment station as claimed in claim 7 wherein said collecting container includes a replaceable filter of hydrophobic material.

10. A dental treatment station as claimed in claim 7 wherein said charging unit further comprises an evaporation device for removing the liquid from the debris.

11. A dental treatment station as claimed in claim 7 wherein said charging unit further comprises a microwave generator for removing the liquid from the debris.

* * * * *